US009700946B2

(12) United States Patent
Andrews

(10) Patent No.: US 9,700,946 B2
(45) Date of Patent: Jul. 11, 2017

(54) APPARATUS AND METHOD FOR PREPARING A SAMPLE FROM COMPONENTS INTERNAL TO A TIRE

(71) Applicant: Bridgestone Americas Tire Operations, LLC, Nashville, TN (US)

(72) Inventor: Katharine M. Andrews, Medina, OH (US)

(73) Assignee: Bridgestone Americas Tire Operations, LLC, Nashville, TN (US)

( * ) Notice: Subject to any disclaimer, the term of this patent is extended or adjusted under 35 U.S.C. 154(b) by 116 days.

(21) Appl. No.: 14/439,994

(22) PCT Filed: Dec. 18, 2013

(86) PCT No.: PCT/US2013/076174
§ 371 (c)(1),
(2) Date: Apr. 30, 2015

(87) PCT Pub. No.: WO2014/100208
PCT Pub. Date: Jun. 26, 2014

(65) Prior Publication Data
US 2015/0290723 A1    Oct. 15, 2015

Related U.S. Application Data

(60) Provisional application No. 61/739,223, filed on Dec. 19, 2012.

(51) Int. Cl.
*B23C 3/00* (2006.01)
*G01M 17/02* (2006.01)
*G01N 1/04* (2006.01)

(52) U.S. Cl.
CPC .............. *B23C 3/00* (2013.01); *G01M 17/02* (2013.01); *G01N 1/04* (2013.01); *G01N 2203/0298* (2013.01)

(58) Field of Classification Search
CPC  B23C 3/00; G01M 17/02; G01N 1/04; G01N 2203/0298
(Continued)

(56) References Cited

U.S. PATENT DOCUMENTS 2,925,125 A    2/1960  Curry
4,036,275 A *  7/1977  Branick .................. B24B 5/366
                                                    157/13
(Continued)

FOREIGN PATENT DOCUMENTS

CN    2064277 U    10/1990
CN    2508940 Y    9/2002
(Continued)

OTHER PUBLICATIONS

Translation of KR 20050036215.*
(Continued)

*Primary Examiner* — Natalie Huls
*Assistant Examiner* — Monica S Young
(74) *Attorney, Agent, or Firm* — Meredith E. Hooker; John M. Skeriotis

(57) ABSTRACT

Provided is a method for preparing a test sample comprising, providing a CNC machine; providing a cured tire comprising, a tire component at least partially covered by an external component, or a tire component at least partially covered by an internal component; and using the CNC machine to separate the tire component from the cured tire by either removing part of the external component, or removing part of the internal component.

14 Claims, 3 Drawing Sheets

(58) Field of Classification Search
USPC .................................................... 73/864.41
See application file for complete search history.

(56) References Cited

U.S. PATENT DOCUMENTS

| | | | | |
|---|---|---|---|---|
| 4,782,881 | A * | 11/1988 | Brinkley | B29D 30/68 157/13 |
| 5,005,628 | A * | 4/1991 | Kinuhata | B29D 30/68 157/13 |
| 5,065,804 | A * | 11/1991 | Kinuhata | B23D 35/008 157/13 |
| 5,144,996 | A * | 9/1992 | Kinuhata | B29D 30/68 157/13 |
| 2001/0045125 | A1 | 11/2001 | Alexander | |
| 2004/0074292 | A1 * | 4/2004 | Irwin | B23C 3/00 73/146 |
| 2011/0226050 | A1 | 9/2011 | Nakayama et al. | |

FOREIGN PATENT DOCUMENTS

| | | |
|---|---|---|
| CN | 2697625 Y | 5/2005 |
| CN | 201324911 Y | 10/2009 |
| CN | 201385243 Y | 1/2010 |
| CN | 101774037 A | 7/2010 |
| CN | 202138131 U | 2/2012 |
| JP | 63281832 A | 5/1987 |
| KR | 20050036215 A * | 4/2005 |
| KR | 1020050036215 A | 4/2005 |
| KR | 200458829 Y1 * | 2/2012 |
| KR | 1020120092965 A | 8/2012 |

OTHER PUBLICATIONS

Translation of 200458829 Y1.*
Ahn, Jae Yul, International Search Report with Written Opinion from PCT/US2013/076174, 12 pp. (Apr. 12, 2014).

* cited by examiner

APPARATUS AND METHOD FOR PREPARING A SAMPLE FROM COMPONENTS INTERNAL TO A TIRE

TECHNICAL FIELD

The present subject matter relates generally to a tire testing. More, specifically, the present subject matter relates to an apparatus and method for preparing a sample from components internal to a tire.

BACKGROUND

It is sometimes desirable to create test samples from internal components of a tire. Creation of test samples often requires the use of hand tools and user-guided power tools to extract the internal components of a tire. The use of hand tools and user-guided power tools to extract the internal components of a tire can be imprecise and can present safety issue.

Computer numerical control (CNC) machine tools and CNC controlled machining can be more precise than and/or safer than the use of hand tools and user-guided power tools.

It remains desirable to develop methods and apparatus for the create test samples from internal components of a tire to make precision cuts to the components of a tire.

SUMMARY

Provided is a method for preparing a test sample comprising, providing a CNC machine; providing a cured tire comprising, a tire component at least partially covered by an external component, or a tire component at least partially covered by an internal component; and using the CNC machine to separate the tire component from the cured tire by either removing part of the external component, or removing part of the internal component.

DETAILED DESCRIPTION

Reference will be made to the drawings, FIGS. 1-5, wherein the showings are only for purposes of illustrating certain embodiments of an apparatus and method for preparing a sample from components internal to a tire.

Figure 1:
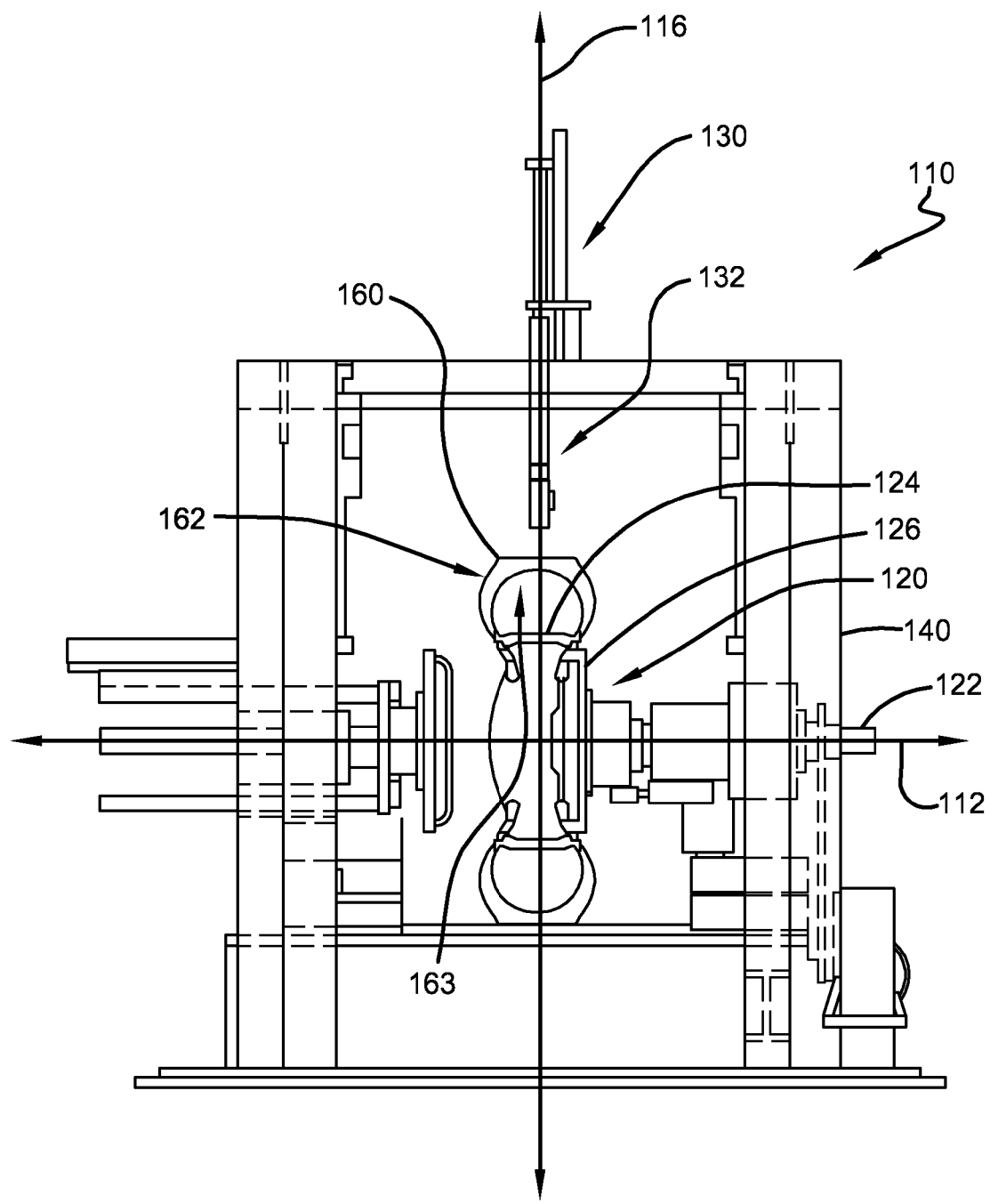
FIG. 1 is a view of a first embodiment of a CNC machine.

Referring now to FIG. 1, an apparatus 110 adapted to prepare an internal tire component sample may comprise a tire engagement component 120, and a CNC machine 130. The CNC machine 130 may be engaged with the tire engagement component 120. In the non-limiting implementations shown in FIG. 1, the CNC machine 130 is engaged with the tire engagement component 120 through a frame 140. The frame 140 may be adapted to engage both the CNC machine 130 and the tire engagement component 120 in such a manner as to substantially positively locate the CNC machine 130 with respect to the tire engagement component 120. As used herein, the term substantially positively locate means to provide a positive location having an error less than that of the desired machining process; the positive location error typically being less 0.001 inches. In other non-limiting implementations, the CNC machine 130 may be engaged with the tire engagement component 120 using means acceptable to good engineering judgment.

The tire engagement component 120 may be any sort of apparatus adapted to provide engagement between the CNC machine 130 and the tire 160. In the implementation shown in FIG. 1 the tire engagement component 120 is an apparatus adapted to simultaneously engage the tire 160, and engage, indirectly through frame 140, the CNC machine 130. In certain implementations, the tire engagement component 120 may comprise adaptations such as a motor, rotatable shaft 122, or other apparatus to permit the tire 160 to be selectably rotated or moved with respect to the CNC machine 130 while the tire 160 is engaged with the tire engagement component 120. In certain implementations, the tire engagement component 120 holds the tire 160 in a substantially fixed position and orientation with respect to the CNC machine 130 while the tire 160 is engaged with the tire engagement component 120.

In certain implementations, the tire engagement component 120 may comprise or be adapted to engage with conventional components typically adapted for the engagement of a tire 160 with a vehicle (not shown) or to provide selectable freedom of motion or orientation between a tire 160 with a vehicle (not shown). These conventional components may include, but are not limited to, a wheel 124, a lug nut (not shown), a hub 126, a lug bolt (not shown), and a brake (not shown). In certain implementations, the tire engagement component 120 may comprise or be adapted to engage with conventional components typically adapted for the test testing such as, without limitation, a digital encoder (not shown), and a load cell (not shown).

The CNC machine 130 may be any sort of computer numerical control machine tool. As used herein, CNC machining comprises 5 axis machining, 4 axis machining, and 3 axis machining. The CNC machine 130 may comprise a tool spindle 132 that may be moved with respect to an object to be machined, such as, without limitation, a tire 160. A tool spindle 132 that may be moved with respect to an object to be machined along an X axis 112, a Y axis perpendicular to the X-axis (not shown), and along a Z-axis 116 mutually perpendicular to the X-axis 112 and the Y-axis (not shown). In certain implementations, the tool spindle 132 may be adapted to translate along and rotate about Cartesian coordinates. In certain implementations, the tool spindle 132 may be adapted to translate along and rotate about cylindrical coordinates. In certain implementations, the tool spindle 132 may be adapted to translate along and rotate about spherical coordinates. In the non-limiting implementation shown in FIG. 1, the position of the tool spindle 132 may be driven by motors through a set of step-down gears, by direct-drive stepper motor, or servo motors. While in typical commercial CNC machines closed-loop controls are standard, in some implementations of the present subject matter, open-loop control may also be acceptable if the forces applied are kept small and speeds are not large.

A CNC machine 130 may be adapted to perform any of a large variety of processes including but not limited to milling, punching, plasma cutting, and grinding.

Tire 160 may be any sort of tire. The tire 160 may be pneumatic, non-pneumatic, run-flat, radial, or bias. The tire 160 may be a passenger tire, a light truck tire, a truck or bus tire, an agricultural tire, or other sort of tire. The tire 160 may be a cured tire, or a uncured tire. In the non-limiting implementations shown in FIG. 1, tire 160 is a pneumatic tire mounted to the tire engagement component 120 and inflated to some desired pressure.

Figure 2:
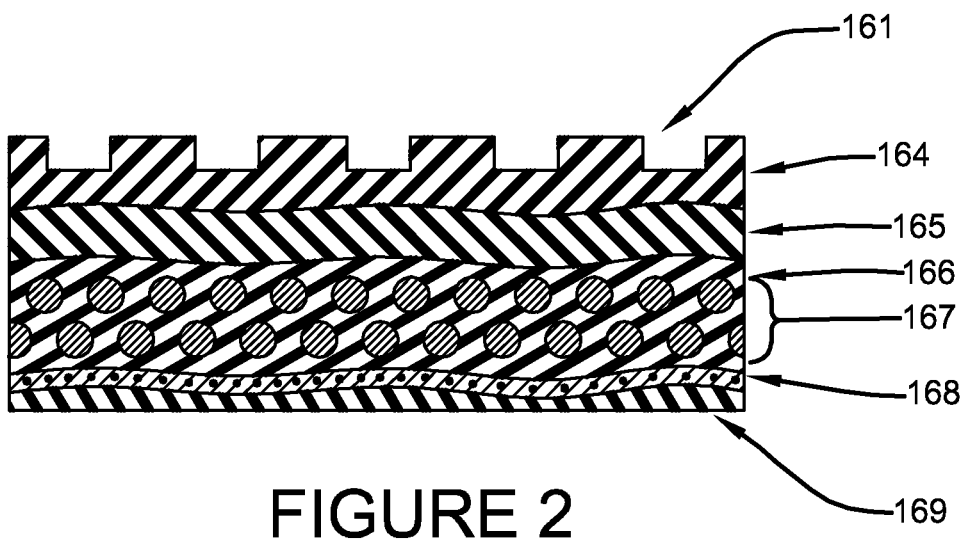
FIG. 2 is a portion of a cross-section of a tire tread.

As shown in the non-limiting embodiment shown in FIG. 1, the tire 160 may comprise an external component 162 and an internal component 163. The non-limiting embodiment shown in FIG. 2, is a cross-section of a tire 160 showing the tire components 161 thereof. In the non-limiting embodiment shown in FIG. 2, the tire components 161 comprise tread 164 which covers subtread 165 which covers a third compound 166 which covers a belt package 167 which covers a body ply compound with fabric 168 which covers an innerliner 169. As shown in FIG. 2, tread 164 is the most external of the components while the innerliner 169 is the most internal of the components. In some embodiments a component that covers another component may provide full coverage, and in others it may provide only partial coverage.

In order to prepare an internal tire component sample, it may be desirable to section out an individual tire component 161 or a sub-set of tire components 161. To section out a desired component 161 is to remove all or substantially all of the engaged components or materials that are not the desired component 161. Similarly, to section out a desired sub-set of tire components 161 is to remove all or substantially all of the engaged components or materials that are not the desired sub-set of tire components 161. Sectioning out a desired tire component 161 or a sub-set of tire components 161 requires a material removal process such as, without limitation cutting or milling to remove the engaged components or materials that are not the desired component 161 or a sub-set of tire components 161. A CNC machine may be usable for very precise material removal processes so as to be usable to prepare an internal tire component sample of a very specific geometry.

Figure 3:
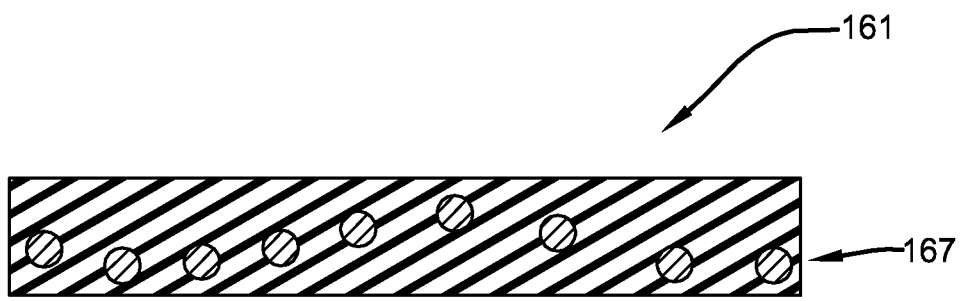
FIG. 3 is a portion of a cross-section of a tire tread.

As shown in the non-limiting embodiment shown in FIGS. 2 and 3, the tire components 161, tread 164, subtread 165, third compound 166, belt package 167, body ply compound with fabric 168, and innerliner 169, may follow a complex path, that is a path that is undulating or otherwise not straight, either in the plane of the cross-section shown in FIG. 2, transverse to the plane of the cross-section shown in FIG. 2, or both. In order to section out a tire component 161 that follows a complex path, the cutting tool must be able to follow a similarly complex path defining a very precise geometry. Hand cutting methods are sometime not sufficiently precise for such purposes.

Figure 4:
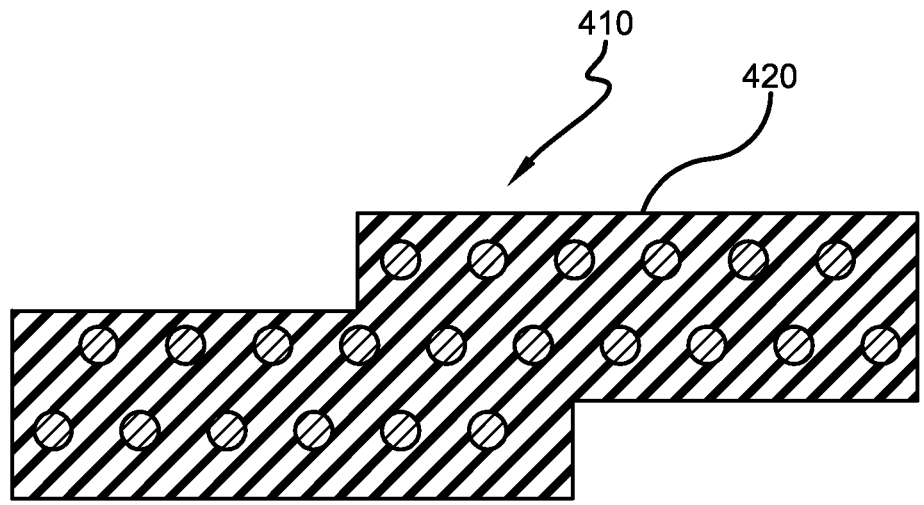
FIG. 4 is a portion of a cross-section of a tire tread.

In the non-limiting embodiment shown in FIG. 4, an internal tire component sample section 410 may be formed by sectioning out tire components 161, such as, without limitation, belt package 167. The internal tire component sample section 410 is defined by a precise geometry identified by the outer surface 420 of the sample section 410.

Figure 5:
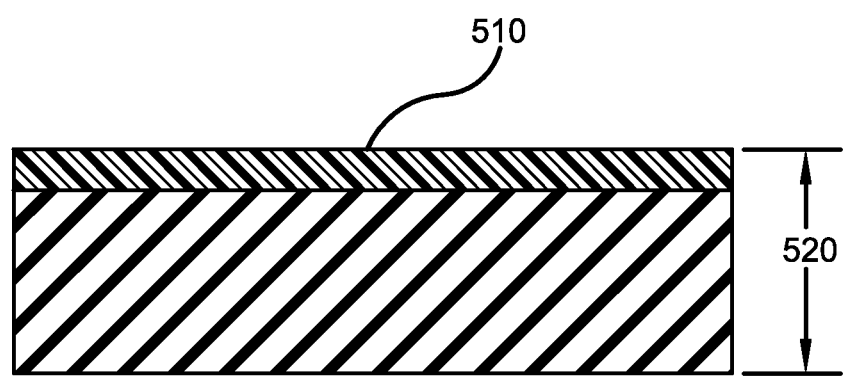
FIG. 5 is a portion of a cross-section of a tire tread.

FIG. 5 shows a non-limiting embodiment of a common test sample 510 of a part of a tire component 161 comprising rubber with a nylon cap. The width dimension 520 of the test sample 510 is 0.5 inch. Cutting test sample 510 by hand with the desired precision would be very difficult, in part, because test sample 510 is so small.

As is noted above, a CNC machine may be usable to prepare an internal tire component sample by section out a tire component 161 as defined by a precise geometry. That is, it is possible to use CNC technology, such as programs, vision systems, and other conventional CNC inputs, in order to obtain required material removal lengths and depths, or to otherwise extract desired individual compounds or components with great precision. Cutting test sample 510 by use of a CNC machine 130 with the desired precision would be very simple even though the test sample 510 is so small.

Accordingly, it may be desirable to use an apparatus 110 comprising a CNC machine 130 to create a test sample 510 from tire components 161 of a tire 160. A test sample 510 of tire components 161 of a tire 160, comprising an external component 162 that at least partially covers tire components 161 or an internal component 163 that at least partially covers tire components 161, may be prepared by providing a CNC machine 130; providing a tire 160; and using the CNC machine 130 to separate the tire components 161 from the tire 160 by remove part of the external component 162 or part of the internal component 163.

While the apparatus and method for preparing a sample from components internal to a tire has been described above in connection with certain embodiments, it is to be understood that other embodiments may be used or modifications and additions may be made to the described embodiments for performing the same function of the apparatus and method for preparing a sample from components internal to a tire without deviating therefrom. Further, the apparatus and method for preparing a sample from components internal to a tire may include embodiments disclosed but not described in exacting detail. Further, all embodiments disclosed are not necessarily in the alternative, as various embodiments may be combined to provide the desired characteristics. Variations can be made by one having ordinary skill in the art without departing from the spirit and scope of the apparatus and method for preparing a sample from components internal to a tire. Therefore, the apparatus and method for preparing a sample from components internal to a tire should not be limited to any single embodiment, but rather construed in breadth and scope in accordance with the recitation of the attached claims.

What is claimed is:

1. A tire test sample preparation apparatus comprising:
a CNC machine
having a cutting tool, the CNC machine being adapted to operate the cutting tool to remove a tire test sample from an associated cured pneumatic tire mounted to an associated wheel, the associated tire having
an external component, and
an internal component underneath the external component;
having a tool spindle movable with respect to the associated tire, the tool spindle being adapted to hold the cutting tool;
a tire engagement component adapted to operationally engage the associated tire through the associated wheel to the CNC machine,
the tire engagement component being adapted to rotate the associated tire with respect to the CNC machine before the CNC machine removes the tire test sample from the associated tire;
the tire engagement component being adapted to hold the associated tire in a substantially fixed position and orientation with respect to the CNC machine while the CNC machine operates the cutting tool;
wherein the tire test sample includes at least a portion of a belt package;
wherein the apparatus is further adapted to use the CNC machine to undercut the test sample by removing at least part of the internal component underneath the external component while leaving the covering external component intact; and,
the cutting tool is adapted to follow an undulating path.

2. The apparatus of claim 1 wherein the CNC machine separates the tire test sample with a width of approximately 0.5 inches.

3. The apparatus of claim 1, wherein the CNC machine is adapted to use a cylindrical or spherical coordinate system.

4. The apparatus of claim 3, wherein
the CNC machine is operationally engaged with an open-loop control system;
the CNC machine has a vision system operationally engaged therewith, the vision system being adapted to provide required material removal lengths and depths as CNC inputs to direct cutting of the test sample;
the CNC machine is operationally adapted for undercutting the test sample by removing at least part of the internal component underneath the external component while leaving the covering external component intact; and the CNC machine is operationally adapted to cut one or more belt components of the tire.

5. The apparatus of claim 1, wherein the CNC machine is operationally engaged with an open-loop control system.

6. The apparatus of claim 1, wherein the CNC machine has a vision system operationally engaged therewith, the vision system being adapted to provide required material removal lengths and depths as CNC inputs to direct cutting of the test sample.

7. The apparatus of claim 1, wherein the CNC machine is operationally adapted to undercutting the test sample by removing at least part of the internal component underneath the external component while leaving the covering external component intact.

8. A method for preparing a tire test sample comprising the steps of:
(A) providing a tire test sample preparation apparatus having
a CNC machine
having a cutting tool, the CNC machine being adapted to operate the cutting tool to remove a tire test sample from an associated cured pneumatic tire mounted to an associated wheel, the associated tire having
an external component, and
an internal component underneath the external component;
having a tool spindle movable with respect to the associated tire, the tool spindle being adapted to hold the cutting tool,
a tire engagement component adapted to operationally engage the associated tire through the associated wheel to the CNC machine,
the tire engagement component being adapted to rotate the associated tire with respect to the CNC machine before the CNC machine removes the tire test sample from the associated tire,
the tire engagement component being adapted to hold the associated tire in a substantially fixed position and orientation with respect to the CNC machine while the CNC machine operates the cutting tool, and
wherein the cutting tool is adapted to follow an undulating path;
(B) providing a wheel;
(C) providing a cured pneumatic tire including a belt package;
(D) mounting the cured pneumatic tire on the wheel;
(E) operationally engaging the tire through the associated wheel to a tire engagement component and the CNC machine;
(F) rotating the tire with respect to the CNC machine using the tire engagement component;
(G) using the tire engagement component to hold the tire in a substantially fixed position and orientation with respect to the CNC machine;
(H) operating the cutting tool by moving the tool spindle and moving the cutting tool along an undulating path with respect to the tire to remove a tire test sample from the tire, wherein the tire test sample includes include at least portion of the belt package;
(I) wherein the method further includes using the CNC machine to undercut the test sample by removing at least part of the internal component underneath the external component while leaving the covering external component intact; and,
(J) testing the tire test sample.

9. The method of claim 8, wherein the CNC machine uses a cylindrical or spherical coordinate system.

10. The method of claim 9, wherein
the CNC machine is operationally engaged with an open-loop control system;
wherein the CNC machine has a vision system operationally engaged therewith, and, using the vision system to provide required material removal lengths and depths as CNC inputs to direct cutting of the test sample;
using the CNC machine to undercut the test sample by removing at least part of the internal component underneath the external component while leaving the covering external component intact; and
using the CNC machine to cut one or more belt components of the tire.

11. The method of claim 8, wherein the CNC machine uses an open-loop control system.

12. The method of claim 8,
wherein the CNC machine has a vision system operationally engaged therewith; and,
using the vision system to provide required material removal lengths and depths as CNC inputs to direct cutting of the test sample.

13. The method of claim 8, further comprising using the CNC machine to undercut the test sample by removing at least part of the internal component underneath the external component while leaving the covering external component intact.

14. A method for preparing a tire test sample comprising the steps of:
(A) providing a tire test sample preparation apparatus having
a CNC machine
having a cutting tool, the CNC machine being adapted to operate the cutting tool to remove a tire test sample from an associated cured pneumatic tire mounted to an associated wheel, the associated tire having
an external component, and
an internal component underneath the external component;
having a tool spindle movable with respect to the associated tire, the tool spindle being adapted to hold the cutting tool,
a tire engagement component adapted to operationally engage the associated tire through the associated wheel to the CNC machine,
the tire engagement component being adapted to rotate the associated tire with respect to the CNC machine before the CNC machine removes the tire test sample from the associated tire, the tire engagement component being adapted to hold the associated tire in a substantially fixed position and orientation with respect to the CNC machine while the CNC machine operates the cutting tool, and wherein the cutting tool is adapted to follow an undulating path;

(B) providing a wheel;
(C) providing a cured pneumatic tire including a belt package;
(D) mounting the cured pneumatic tire on the wheel;
(E) operationally engaging the tire through the associated wheel to a tire engagement component and the CNC machine;
(F) rotating the tire with respect to the CNC machine using the tire engagement component;
(G) using the tire engagement component to hold the tire in a substantially fixed position and orientation with respect to the CNC machine;
(H) operating the cutting tool by moving the tool spindle and moving the cutting tool along an undulating path with respect to the tire to remove a tire test sample from the tire, wherein the tire test sample includes include at least portion of the belt package;
(I) testing the tire test sample; and wherein the CNC machine uses a cylindrical or spherical coordinate system;

wherein the CNC machine uses an open-loop control system;

wherein the CNC machine has a vision system operationally engaged therewith; wherein the method further includes using the vision system to provide required material removal lengths and depths as CNC inputs to direct cutting of the test sample; and wherein the method further includes using the CNC machine to undercut the test sample by removing at least part of the internal component underneath the external component while leaving the covering external component intact.

* * * * *